US011180724B2

(12) United States Patent
Lee et al.

(10) Patent No.: US 11,180,724 B2
(45) Date of Patent: Nov. 23, 2021

(54) MICROFLUIDIC PRESSURE REGULATOR FOR ROBUST HYDROGEL LOADING WITHOUT BURSTING

(71) Applicant: The Regents of the University of California, Oakland, CA (US)

(72) Inventors: Abraham P. Lee, Irvine, CA (US); Xiaolin Wang, Shanghai (CN); Duc Phan, Fountain Valley, CA (US); Christopher C. W. Hughes, Irvine, CA (US); Steven C. George, St. Louis, MO (US)

(73) Assignee: The Regents of the University of California, Oakland, CA (US)

(*) Notice: Subject to any disclaimer, the term of this patent is extended or adjusted under 35 U.S.C. 154(b) by 160 days.

(21) Appl. No.: 15/333,183

(22) Filed: Oct. 24, 2016

(65) Prior Publication Data
US 2017/0130187 A1   May 11, 2017

Related U.S. Application Data

(60) Provisional application No. 62/245,829, filed on Oct. 23, 2015.

(51) Int. Cl.
C12M 3/06         (2006.01)
C12M 1/34         (2006.01)
(Continued)

(52) U.S. Cl.
CPC ....... *C12M 23/16* (2013.01); *B01L 3/502738* (2013.01); *C12M 21/08* (2013.01);
(Continued)

(58) Field of Classification Search
CPC ....... B01L 2200/027; B01L 2200/0647; B01L 2200/0673; B01L 2300/0681;
(Continued)

(56) References Cited

U.S. PATENT DOCUMENTS

| 2012/0196280 A1* | 8/2012 | Karlsen | B01L 3/5027 435/6.1 |
| 2014/0057311 A1* | 2/2014 | Kamm | B01L 3/502753 435/29 |
| 2016/0091510 A1* | 3/2016 | Di Tullio | B01L 3/502715 435/287.1 |

OTHER PUBLICATIONS

D. H. Lee, C. Y. Bae, S. Kwon and J. K. Park, Lab Chip, 2015, 15(11), 2379.
(Continued)

*Primary Examiner* — Dean Kwak
(74) *Attorney, Agent, or Firm* — Brooks Kushman P.C.

(57) ABSTRACT

A pressure regulator module for a chip-based microfluidic platform is provided. The module includes a microfluidic channel for passing flowable material from the inlet region through the outlet region and into a downstream compartment; one or more microvalves fluidly connected to the microfluidic channel and upstream of the outlet region; and one or more reservoirs fluidly connected to the microvalves, for receiving flowable material diverted by the microvalves, where a flow of flowable material passing from the inlet region toward the downstream compartment is at least partially diverted by the microvalves into the reservoirs as a result of a pressure increase in the microfluidic channel. In some versions, the microvalves are capillary burst valves. A microfluidic chip containing the module and a method of using the module are provided.

5 Claims, 20 Drawing Sheets

(51) Int. Cl.
*B01L 3/00* (2006.01)
*C12M 1/00* (2006.01)
*C12M 3/00* (2006.01)

(52) U.S. Cl.
CPC ............ *C12M 29/10* (2013.01); *C12M 41/40* (2013.01); *B01L 3/502761* (2013.01); *B01L 2200/0647* (2013.01); *B01L 2300/0864* (2013.01); *B01L 2400/0688* (2013.01)

(58) Field of Classification Search
CPC ..... B01L 2300/0864; B01L 2400/0487; B01L 2400/0622; B01L 2400/0688; B01L 3/502715; B01L 3/502738; B01L 3/502753; B01L 3/502761; C12M 21/08; C12M 23/16; C12M 41/40; C12M 29/10; G01N 2035/00158; G01N 2035/1034; G01N 30/10; G01N 35/10
USPC .......... 422/502–504, 522, 113, 114, 81, 536, 422/537; 436/180; 435/305.1, 305.2, 435/289.1
See application file for complete search history.

(56) References Cited

OTHER PUBLICATIONS

V. Vickerman, J. Blundo, S. Chung and R. Kamm, Lab Chip, 2008, 8(9), 1468.
C. Y. Chan, P.-H. Huang, F. Guo, X. Ding, V. Kapur, J. D. Mai, P. K. Yuen and T. J. Huang, Lab Chip, 2013, 13(24), 4697.
S. N. Bhatia and D. E. Ingber, Nat. Biotechnol., 2014, 32(8), 760.
D. Huh, Y. S. Torisawa, H. J. Kim and D. E. Ingber, Lab Chip, 2012, 12(12), 2156.
S. Kim, H. Lee, M. Chung and N. L. Jeon, Lab Chip, 2013, 13(8), 1489.
Y. Zheng, J. Chen, M. Craven, N. W. Choi, S. Totorica, A. Diaz-Santana, P. Kermani, B. Hempstead, C. Fischbach-Teschl and J. A. López, Proc. Natl. Acad. Sci. U. S. A., 2012, 109(24), 9342.
Y. H. Hsu, M. L. Moya, C. C. Hughes, S. C. George and A. P. Lee, Lab Chip, 2013, 13(1), 81.
Y. H. Hsu, M. L. Moya, C. C. Hughes, S. C. George and A. P. Lee, Lab Chip, 2013, 13(15), 2990.
J. H. Yeon, H. R. Ryu, M. Chung, Q. P. Hu and N. L. Jeon, Lab Chip, 2012, 12(16), 2815.
M. B. Chen, J. A. Whisler, J. S. Jeon and R. D. Kamm, Integr. Biol., 2013, 5(10), 1262.
C. P. Huang, J. Lu, H. Seon, A. P. Lee, L. A. Flanagan, H. Y. Kim, A. J. Putnam and N. L. Jeon, Lab Chip, 2009, 9(12), 1740.
A. K. Au, H. Lai, B. R. Utela and A. Folch, Micromachines, 2011, 2(2), 179.
M. L. Moya, Y. H. Hsu, A. P. Lee, C. C. Hughes and S. C. George, Tissue Eng., Part C, 2013, 19(9), 730.
X. Wang, D. T. Phan, A. Sobrino, S. C. George, C. C. Hughes and A. P. Lee, Lab Chip, 2016, 16(2) 282.
M. Rhee, Y. K. Light, S. Yilmaz, P. D. Adams, D. Saxena, R. J. Meagher and A. K. Singh, Lab Chip, 2014, 14(23), 4533.
K. W. Oh, K. Lee, B. Ahn and E. P. Furlani, Lab Chip, 2012, 12(3), 515.
D. J. Beebe, G. A. Mensing and G. M. Walker, Annu. Rev. Biomed. Eng., 2002, 4(1), 261.
H. Cho, H. Y. Kim, J. Y. Kang and T. S. Kim, J. Colloid Interface Sci., 2007, 306(2), 379.
I. K. Zervantonakis, S. K. Hughes-Alford, J. L. Charest, J. S. Condeelis, F. B. Gertler and R. D. Kamm, Proc. Natl. Acad. Sci. U. S. A., 2012, 109(34), 13515.
J. M. Melero-Martin, Z. A. Khan, A. Picard, X. Wu, S. Paruchuri and J. Bischoff, Blood, 2007, 109(11), 4761.
L. F. Alonzo, M. L. Moya, V. S. Shirure and S. C. George, Lab Chip, 2015, 15(17), 3521.

\* cited by examiner

| (A) Safety microvalve / Flow rate | Width: 55 μm | Width: 85 μm |
|---|---|---|
| 50 μL/min | S1-B0, S2-B0 | S1-B0, S2-B1 |
| 100 μL/min | S1-B0, S2-B1 | S1-B0, S2-B2 |
| 130 μL/min | S1-B0, S2-B2 | S1-B1, S2-B2 |
| 320 μL/min | S1-B1, S2-B2 | S1-B2, S2-B2 |

FIG. 4

| Flow rate | 100μm wide perfusion microvalve | Gel interface |
|---|---|---|
| 20 μL/min | S1-B0, S2-B0 | |
| 45 μL/min | S1-B0, S2-B1 | |
| 50 μL/min | S1-B0, S2-B2 | |
| 55 μL/min | S1-B1, S2-B1 | |
| 70 μL/min (volume: 10 μL) | S1-B2, S2-B2 | |
| 120 μL/min (volume: 10 μL) | S1-B2, S2-B2 | |

FIG. 5

MICROFLUIDIC PRESSURE REGULATOR FOR ROBUST HYDROGEL LOADING WITHOUT BURSTING

CROSS-REFERENCE TO RELATED APPLICATIONS

This application claims the benefit of Provisional Patent Application No. 62/245,829, filed on Oct. 23, 2015, which is incorporated by reference herein.

STATEMENT REGARDING FEDERALLY SPONSORED RESEARCH OR DEVELOPMENT

This invention was made with Government support under Grant No. NS080698 from the National Institutes of Health. The Government has certain rights in this invention.

BACKGROUND

Field of the Invention

The invention relates to microfluidic devices and pressure regulators.

Related Art

In recent years, 3D cell culture models have attracted much attention because they can better mimic the in vivo microphysiological environment by incorporating various cell types into hydrogels, including native extracellular matrices (ECM), for long-term cell culture.[1] By integrating 3D hydrogels into microfluidic chips, additional parameters of the microenvironment such as dynamic mechanical cues (e.g. fluid shear stress, interstitial fluid flow, etc.) or spatiotemporal chemical gradients (e.g. growth factor gradients) can be precisely controlled.[2] These sophisticated microfluidic cell culture systems can facilitate the formation of 3D microtissues with specific physiological functions such that we are now beginning to create "organ-on-a-chip" models.[3-5]

In order to provide an avenue for cells to access nutrients and oxygen as well as for waste removal, development of perfusion-based 3D cell cultures with physiological flow through tissue interstitial space has become critical.[6-8] The most commonly used method is to establish fluid flow by setting up two microfluidic channels adjacent to a tissue chamber seeded with cell-ECM suspension.[9-11] In this geometry it is critical that the cell-ECM mixture be confined inside the tissue chamber without leaking into the adjacent microfluidic channels, which would lead to flow obstruction. Conversely, the contact surface between the fluid inside the microfluidic channel and the cell-ECM suspension inside the tissue chamber should be sufficient for biotransportation across the microtissue. Although micro-pillar arrays and other microstructures functioning as microvalves can prevent gel bursting to a certain extent,[12,13] operation failure often occurs due to internal pressure transients exceeding the burst pressure of the air-cell/ECM interface during loading. Use of a syringe pump, where the dispensed volume and the applied flow rate can be more finely controlled, can improve reproducibility over manual loading, however, it is cumbersome to connect the syringe with each microfluidic chip via tubing, and bubbles may easily be generated when connecting and removing tubing, making it undesirable for high-throughput applications. In addition, gel loading with syringe pumps is unsuitable for certain hydrogels that require rapid mixing with a catalytic reagent to fully polymerize. Due to their flexible and easy operation micropipettors are the preferred alternative for hydrogel loading. However, with manual operation it is difficult to achieve constant and consistent flow rates, resulting in pressure fluctuations and gel bursting.

SUMMARY

In various embodiments, a microfluidic pressure regulator is provided that allows for reproducible gel loading without the risk of gel overflow into the microfluidic channels.

In one aspect, a pressure regulator module for a chip-based microfluidic platform is provided. The module includes:

a microfluidic channel including an inlet region and an outlet region downstream of the inlet region, said channel for passing flowable material from the inlet region through the outlet region and into a downstream compartment;

one or more microvalves fluidly connected to the microfluidic channel and disposed upstream of the outlet region, said microvalves for releasing pressure in the microfluidic channel, wherein each microvalve has an open state permitting flowable material to pass through said microvalve and a closed state preventing flowable material from passing through said microvalve, and wherein each microvalve in its open state diverts flowable material from the microfluidic channel; and one or more reservoirs fluidly connected to the microvalves, for receiving flowable material diverted by the microvalves;

wherein a flow of flowable material passing from the inlet region toward the downstream compartment is at least partially diverted by at least one of the microvalves into at least one of the reservoirs as a result of a pressure increase in the microfluidic channel.

In some embodiments of the pressure regulator module, the one or more microvalves are capillary burst valves. In some embodiments, each capillary burst valve width affects the sensitivity and working range of the pressure regulator module.

In another aspect, a chip-based microfluidic platform is provided. The platform includes: one or more compartments, with each compartment including one or more fluidly connected tissue chambers for culturing cells or microtissues; and the pressure regulator module fluidly connected by the outlet region to one or more of the compartments.

In some embodiments of the platform, the one or more microvalves are capillary burst valves. In some embodiments: a) each tissue chamber includes at least two capillary burst valves for perfusing nutrients through the tissue chamber, and the capillary burst valves of the pressure regulator have lower burst pressures than the capillary burst valves of the tissue chambers; b) the tissue chambers contain flowable material that forms an air-flowable material interface at each capillary burst valve of the tissue chambers, and diversion of flowable material into the reservoirs maintains each interface; c) the one or more tissue chambers is a plurality of tissue chambers arranged in different layers; d) each capillary burst valve width affects the sensitivity and working range of the pressure regulator module; or e) any combination of a)-d).

In a further aspect, a method of loading a flowable material into a compartment of an on-chip microfluidic platform is provided. The method includes: passing a flowable material from an inlet region of a microfluidic channel to a downstream outlet region of the microfluidic channel and into a compartment fluidly connected to the outlet region; and diverting, via one or more microvalves located upstream of the compartment, a part of the flowable material from the microfluidic channel into a reservoir as a result of a pressure increase in the microfluidic channel.

In embodiments of the method: a) the compartment includes one or more fluidly connected tissue chambers for culturing cells or microtissues; b) the one or more microvalves are capillary burst valves; c) the compartment includes one or more fluidly connected tissue chambers for culturing cells or microtissues, and each tissue chamber includes at least two capillary burst valves for perfusing nutrients through the tissue chamber, and the capillary burst valves located upstream of the compartment have lower burst pressures than the capillary burst valves of the tissue chambers; d) the tissue chambers contain flowable material that forms an air-flowable material interface at each capillary burst valve of the tissue chambers, and wherein the diverting of flowable material from the microfluidic channel maintains each interface; or e) any combination of a)-d).

BRIEF DESCRIPTION OF THE DRAWINGS

The patent or application file contains at least one drawing executed in color. Copies of this patent or patent application publication with color drawing(s) will be provided by the Office upon request and payment of the necessary fee.

For a more complete understanding of the present invention, reference is now made to the following descriptions taken in conjunction with the accompanying drawings, in which:

FIG. 5 is a panel showing gel confinement with a 100 μm wide perfusion microvalve. Both the pressure regulator module and the gel interface at the perfusion microvalve were sensitive to the applied flow rate. At higher flow rates, smaller gel volumes (e.g. 10 μL) could effectively prevent gel bursting from the perfusion microvalve with a wide opening.

DETAILED DESCRIPTION

Figure 1A:
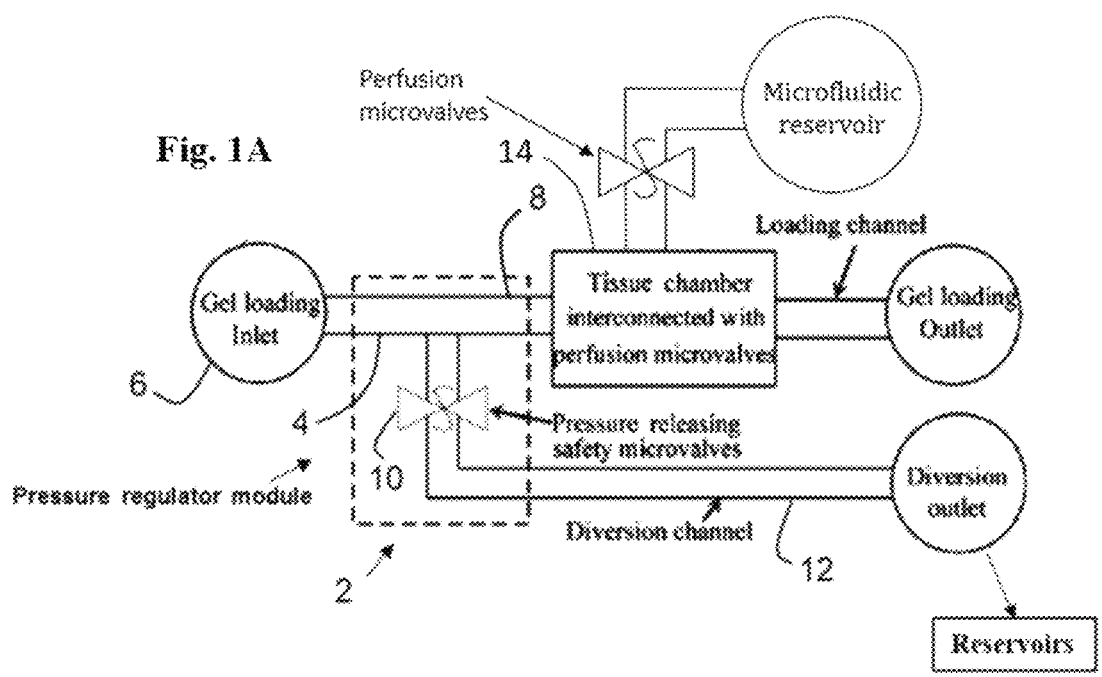
FIG. 1 is a panel showing embodiments of a pressure regulator module design in schematic form. (1A) Schematic of basic pressure regulator module structure. (1B) Example of one pressure regulator design and its integration into a perfusion-based 3D culture device. (1C) A simplified electronic circuit analogy model corresponding to the mechanism of gel loading into the device with pressure regulator module. (1D) Simulation results for the gel loading process in both tissue chamber and pressure regulator module without bursting when the hydraulic pressure inside the gel loading channel is less than the burst pressure of their interconnected capillary burst valves. Color scheme: blue represents gel, red represents air and yellow represents gel/air interface.

Referring to an embodiment in FIG. 1A, a pressure regulator module 2 includes a microfluidic channel 4 that includes an inlet region 6 and an outlet region 8 downstream of the inlet region. One or more microvalves 10 located upstream of the outlet region connect to at least one diversion channel 12. A compartment 14 that includes a tissue chamber is located downstream of the pressure regulator module.

Examples of the microvalve include, but are not limited to, a capillary burst valve and the like.

The pressure regulator module and the chip-based microfluidic platform can be made using standard soft lithography methods or other microfabrication processes. A microfluidic device can be made, for example, of polydimethylsiloxane (PDMS) (Sylgard-184, Dow Corning) by micro-molding from SU-8 patterned silicon wafers using standard soft lithography techniques. A standard SU-8 photolithography process can be used to fabricate micro-molds. First, a layer of SU-8 can be spin-coated onto a Si-wafer (RCA-1 cleaned and 2% HF treated). Then, a single mask photolithography step can pattern a tissue chamber or microfluidic channel, for example. A PDMS layer can be molded on the micro-mold, then de-molded for further processing.

The flowable material is a material that can flow in a microfluidic channel. Examples of flowable materials include, but are not limited to, liquids, cell culture media, cell suspensions, hydrogels, cell-hydrogel mixtures, blood, blood substitutes, and the like.

Examples of hydrogels include, but are not limited to, collagen-based hydrogels, fibrin-based hydrogels, poly(ethylene glycol) ("PEG")-based hydrogels, and the like.

Hydrogel can be prepared, for example, by warming of a collagen type-I solution to promote polymerization, by addition of biological accelerants such as thrombin to fibrinogen, or by photo cross-linking of polymers.

Cell-hydrogel mixtures can be prepared, for example, by warming a collagen type-I solution containing cells to promote polymerization, or by the addition of biological accelerants such as thrombin to mixtures of cells and fibrinogen.

Cells for use in cell-hydrogel mixtures, or for culturing in tissue compartments, include, but are not limited to, stem, endothelial, stromal, epithelial, immune, neuronal, connective, myocardial, hepato, renal, heart, liver, pancreas, muscle, brain, and kidney cells, and any kind of tumor cell. In some embodiments, combinations of these cells can be cultured or included in cell-hydrogel mixtures.

The present invention may be better understood by referring to the accompanying examples, which are intended for illustration purposes only and should not in any sense be construed as limiting the scope of the invention.

EXAMPLE 1

A novel design of an on-chip regulator module with pressure releasing safety microvalves are provided that can effectively maintain the hydraulic pressure inside the gel loading channel within a specified range. The power of this module is validated by its incorporation into a microfluidic platform for culturing 3D vascularized micro-organs (3D-VMO). Using this microfluidic platform both automatic gel loading using a syringe pump and manual gel loading using a micropipettor were tested. These tests demonstrated the module's compatibility with different liquid handling systems and its flexibility to operate in either automatic or manual mode. Experimental results show that the on-chip pressure regulator facilitates robust gel loading into the tissue chamber under multiple different flow rates without bursting into the adjacent microfluidic channels. Finally, the sensitivity and working range of the pressure regulator can be fine-tuned by adjusting the width of the safety microvalves relative to the air-gel interface width. The simplicity of the design allows for easy integration into any microfluidic chip that requires loading of hydrogels.

Materials and Methods
Pressure Regulator Module Design

As shown in FIG. 1A, the on-chip pressure regulator module consists of pressure-releasing capillary burst valves (denoted as safety microvalves) and diversion channels, all based on three basic design principles. First, the burst pressure of safety microvalves in the pressure regulator module should be lower than that of the tissue chamber capillary burst valves (denoted as perfusion microvalves) used for confining loaded gel inside the tissue chambers. This ensures that the safety microvalves will burst first to release redundant gel and regulate the pressure inside the tissue chambers to below the burst pressure of perfusion microvalves. Second, in order to redirect the redundant gel away from the tissue chambers, the pressure regulator module should be positioned upstream of the gel loading channel. Third, the volume of storage space to accommodate the redundant gel should be large enough for a typical single injection volume.

Figure 1B:
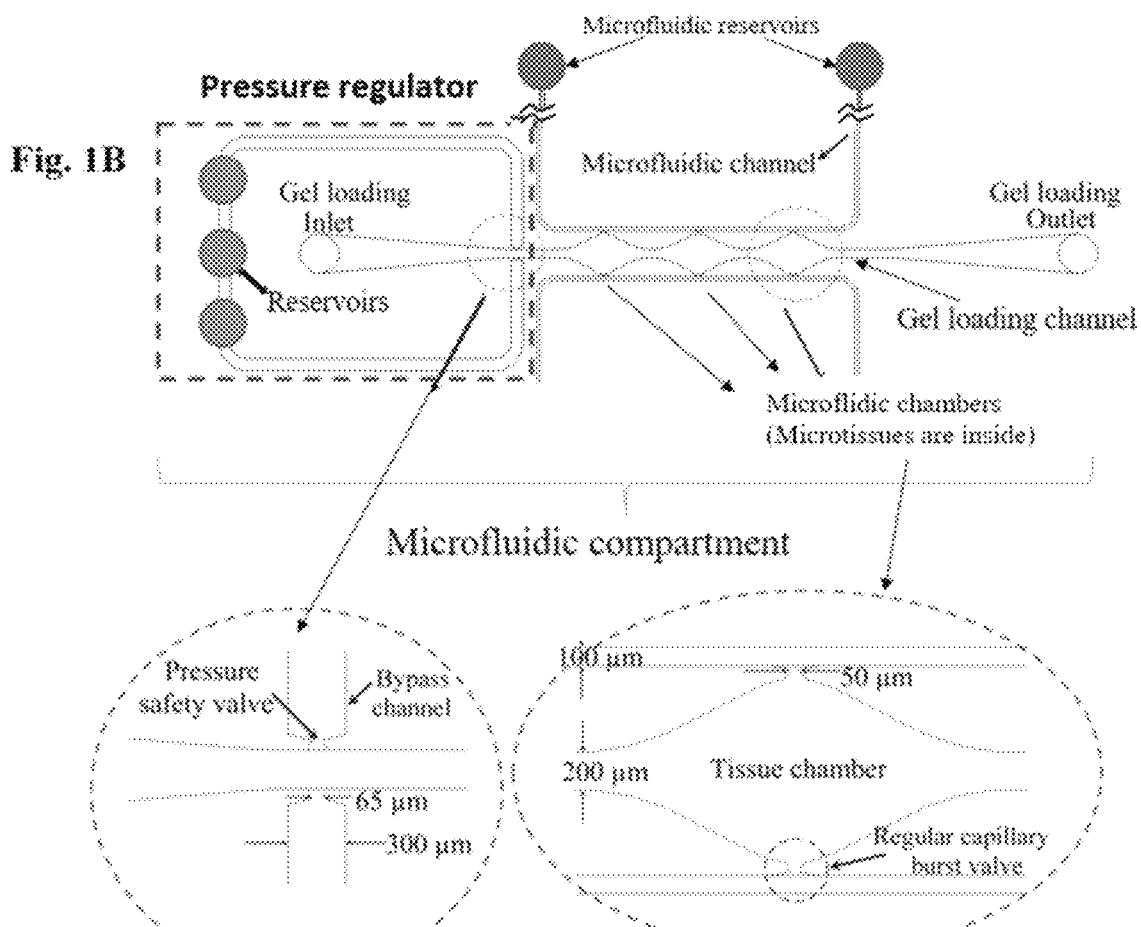
Figure 1:
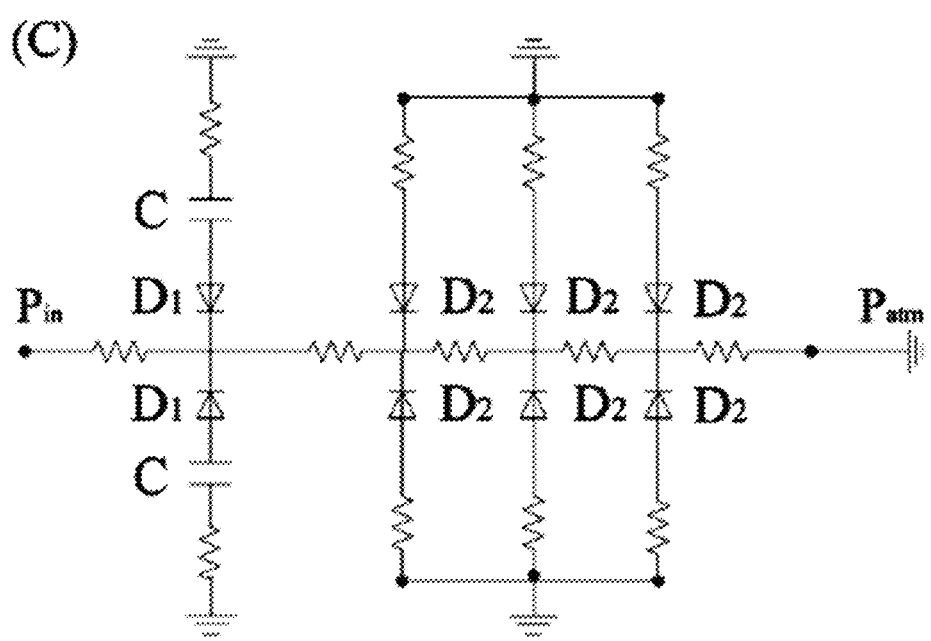
Figure 1:
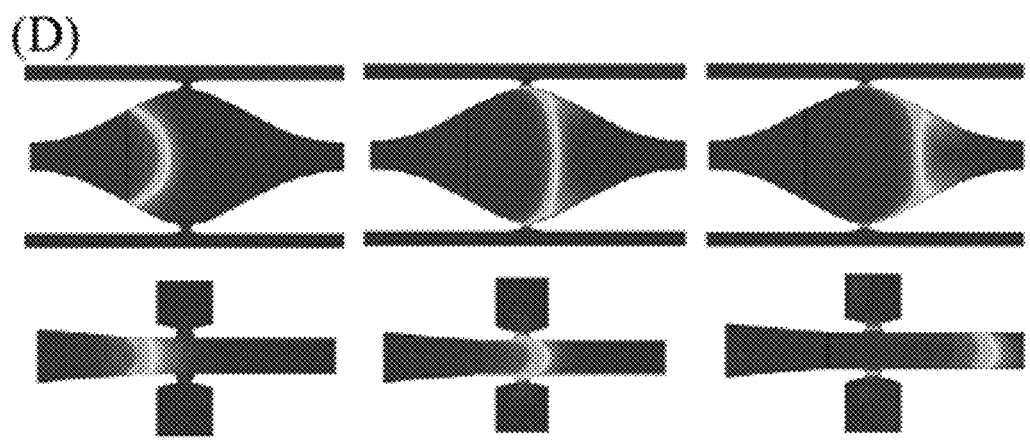

FIG. 1B shows integration of the pressure regulator module design into a perfusion-based microfluidic device for 3D-VMO. The chip design consists of one gel loading channel with three central mm-sized diamond tissue chambers (1×2 mm), each connected to two adjacent microfluidic channels (width: 100 μm) through capillary burst valves (perfusion microvalves, width: 50 μm) that confine the loaded gel inside the tissue chambers.[14,15] The pressure regulator module consists of two capillary burst valves (safety microvalves, width 65 μm) directly connected to the gel loading channel and positioned between the gel loading inlet and the first tissue chamber. A wide microfluidic channel (width: 300 μm) as the diversion channel was utilized to redirect and accommodate the redundant gel. The microfluidic features throughout the device had a constant height of 100 μm.

The entire device can be simulated by a simplified electronic circuit model,[16,17] as shown in FIG. 1C. The external pressure source (Pin) connected to the inlet of the gel loading channel is analogous to a DC voltage source, and the outlet of the gel loading channel can be treated as the floating ground (GND), since it is open to the atmosphere (Patm). The electrical resistance is analogous to the corresponding hydraulic resistance, which can be determined by the channel geometry and dimension. The backward diode represents the capillary burst valve, and its breakdown level corresponds to the burst pressure that varies inversely with the microvalve width. Correspondingly, the maximum backward voltage of D1 (safety microvalve: 65 μm) was smaller than that of D2 (perfusion microvalve: 50 μm). Once the diode breaks down, it would no longer prevent the reverse current, which is analogous to gel bursting. The capacitor C represents the diversion channel to release and accommodate the redundant gel, and its capacitor volume corresponds to the designed volume of this diversion channel.

FIG. 1D shows simulation results for the gel loading process in both the tissue chamber and the pressure regulator module. The "Two-Phase Flow, Laminar, Level Set" application mode in the MEMS module of COMSOL Multiphysics (COMSOL, Burlington, Mass.) was utilized to simulate the moving interface of two immiscible fluid flows by solving the Navier-Stokes equation. The Navier-Stokes equation describes the transport of mass and momentum for fluids with constant density, incorporating surface tension and conservation of mass. The "Level Set" method was utilized to predict the moving interface by using the smooth signed distance function, denoted as $\varphi$ (in air $\varphi=0$, in gel $\varphi=1$, and at interface $\varphi=0.5$). Therefore, the "Level Set" function can be thought of as the volume fraction of gel during the loading process. In the COMSOL simulation, two consecutive computations were executed. First, a smooth initial condition for the "Level Set" variable was calculated, and the solution was stored. Then the transient analysis was started for the time-dependent simulation of fluid motion. The contact angle between the wall and the gel interface as well as the microvalve dimensions were key variables that controlled the gel filling process. Since the inner surface of microfluidic channel made from poly(dimethylsiloxane) (PDMS) is hydrophobic, the injected gel will be confined inside the gel loading channel without bursting into the adjacent microfluidic channels or the diversion channel if the applied hydraulic pressure inside the tissue chambers and pressure regulator module is less than the burst pressure of their corresponding microvalves. Even though the gel precursor viscosity as an important variable contributes to the gel filling speed (fluid motion) during the loading process, the novel pressure regulator module design with high versatility will work for different hydrogel loading regardless of their precursor viscosities.

Gel Loading Model Simplification

Figure 2:
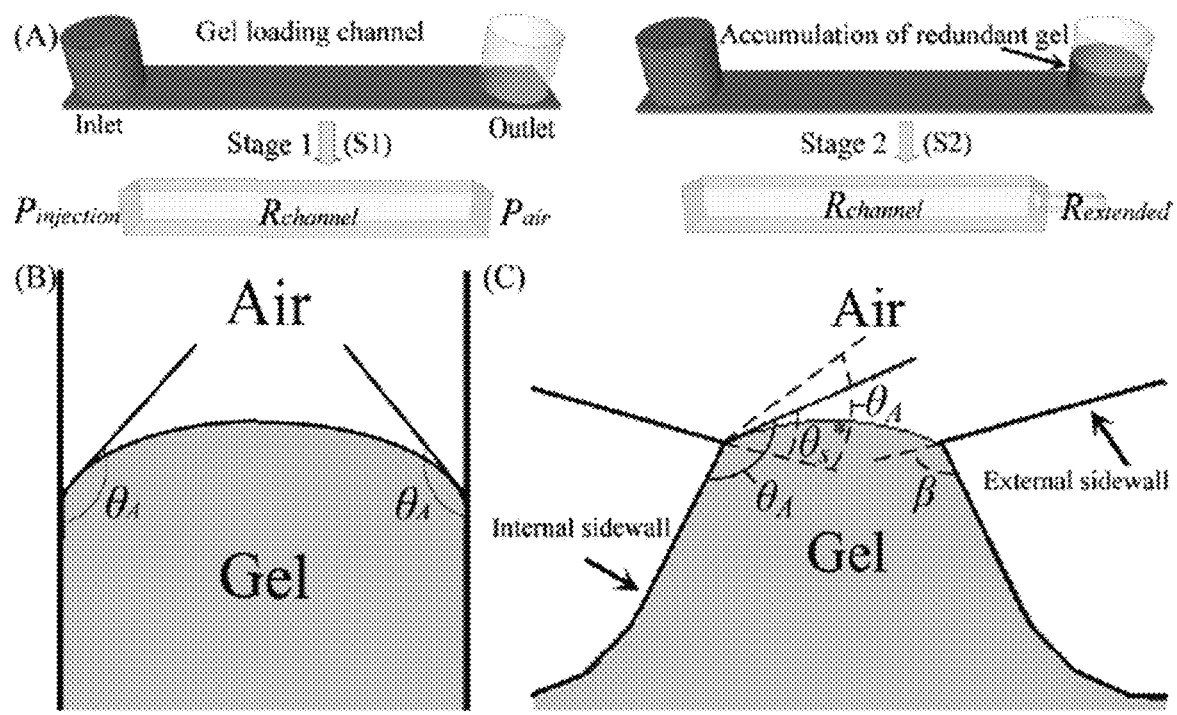
FIG. 2 is a panel of drawings illustrating fluid action. (2A) Simplified model of gel loading along the microfluidic channel, consisting of two stages. (2B) Schematic of gel movement along the loading channel when the contact angles of gel interface with all sidewalls exceed the critical advancing contact angle. (2C) Schematic of the capillary burst valve design with gentle slope and different contact angle of gel interface with sidewalls at the vertices.

The gel loading process usually consists of two stages: the gel moving from inlet to outlet uniformly along the gel loading channel with the same height (S1), and the accumulation of redundant gel at the outlet reservoir (S2), as shown in FIG. 2A. Assuming incompressible laminar flow inside the microfluidic channel, the pressure drop ΔP across the gel loading channel is determined by the product of volume flow rate Q and the fluidic resistance R of the channel (Poiseuille's flow), which is described as:[18]

$$\Delta P = Q * R \quad (1)$$

For the first stage (S1), since the gel is fully distributed along the gel loading channel, its fluidic resistance $R_{channel}$ is solely determined by the channel geometry (i.e. width, height, and whole channel length). Therefore, eqn (1) can be expressed as:

$$\Delta P_{S1} = P_{injection} - P_{air} = Q * R_{channel} \quad (2)$$

where $P_{injection}$ is the pressure applied at the gel loading inlet, and $P_{air}$ is the atmosphere pressure.

However, at the second stage (S2), since there is a certain height of gel accumulated at the outlet reservoir, which can be simplified as an extended channel, the total fluidic resistance of the gel loading channel will increase accordingly. With the increased gel height at the outlet reservoir, the cross section of extended channel with fixed length will become narrow accordingly due to the increased fluidic resistance. Therefore, be simplified as an extended channel, the total fluidic resistance of the gel loading channel will increase accordingly. With the increased gel height at the outlet reservoir, the cross section of extended channel with fixed length will become narrow accordingly due to the increased fluidic resistance. Therefore, the pressure drop along the gel loading channel during the second stage can be expressed as:

$$\Delta P_{S2} = P_{injection} - P_{air} = Q * (R_{channel} + R_{extended}) \quad (3)$$

where $R_{extended}$ is the fluidic resistance of the extended channel.

Therefore, the pressure inside the gel loading channel will build up abruptly as a result of either the high flow rate applied at the first stage (S1), or the dramatically increased fluidic resistance at the second stage (S2). When the internal hydraulic pressure exceeds the burst pressure of microvalves, gel leakage or bursting will occur.

Burst Pressure at Designed Microvalves

To better understand the gel transversing process, it is necessary to characterize the pressure difference exerted on the gel-air interface during the loading process, which can be analyzed by the Young-Laplace equation expressed as:[19]

$$P_{gel} - P_{air} = 2\gamma(\cos\theta_s/w + \cos\delta_v/h) \quad (4)$$

where $P_{gel}$ is the gel pressure inside the interface, γ is surface tension, w and h are width and height of the microfluidic channel where the interface is located, θs is the contact angle formed between the gel interface and sidewalls, and $\delta_v$ is the contact angle of gel interface with the top wall and bottom wall. Therefore, for a given gel with fixed surface tension, the pressure difference across the interface can be adjusted by changing either the microfluidic channel dimensions or the interface curvature with different contact angles.

If the contact angles with all sidewalls exceed the critical advancing contact angle $\theta_A$ (i.e. $\theta_s \geq \theta_A$ and $\theta_v \geq \theta_A$), the interface will burst to induce gel movement, as shown in FIG. 2B. When the gel meniscus is in motion with sufficiently low contact line velocity U and small capillary number $Ca = \mu U/\gamma < 10^{-3}$, where μ is the gel viscosity, we can set its dynamic contact angle $\theta_s \approx \theta_v \approx \theta_A$. Therefore, the pressure difference for the gel bursting interface can be described as:

$$P_{gel\text{-}burst} - P_{air} = -2\gamma(\cos\theta_A/w + \cos\theta_A/h) \quad (5)$$

Due to its single-use feature and simple structure for microfabrication, capillary burst valves are ideal candidates for both safety microvalves at the pressure regulator module and perfusion microvalves at the tissue chambers. Capillary burst valves are characterized by the abrupt change of fluid contact angle to form the high energy meniscus. The increased capillary resistance can be accomplished by the abrupt change of either channel geometry or surface chemistry.[13] For geometrical capillary burst valves, a sudden diverging section of microstructure is normally designed to trap the gel meniscus at the point of expansion. As shown in FIG. 2C, the expanded external sidewall with gentle slope is utilized as the capillary burst valve in our design. When the meniscus approaches the external sidewall, its contact angle reduces from $\theta_A$ to $\theta^* = \theta_A - \beta$, where β is the angle between the internal sidewall and the external sidewall, thus the gel stops instantly. The gel interface will bulge gradually as the pressure builds up, until its contact angle with the external sidewall increases to $\theta_A$, which also means that the contact angle with the internal sidewall increases up to $\theta^*_A = \theta_A + \beta$. It is noted that the maximum contact angle for a liquid meniscus cannot exceed 180°, thus the critical bursting contact angle with the internal sidewall for the capillary burst valve should be $\theta_A^* = \min\{\theta_A + \beta, 180°\}$. Therefore, the burst pressure for our designed microvalves $P_{valve\text{-}burst}$ can be expressed as:

$$P_{valve\text{-}burst} - P_{air} = -2\gamma(\cos\theta^*_A/w + \cos\theta_A/h) \quad (6)$$

Gel Interface Control at the Perfusion Microvalve

Figure 8:
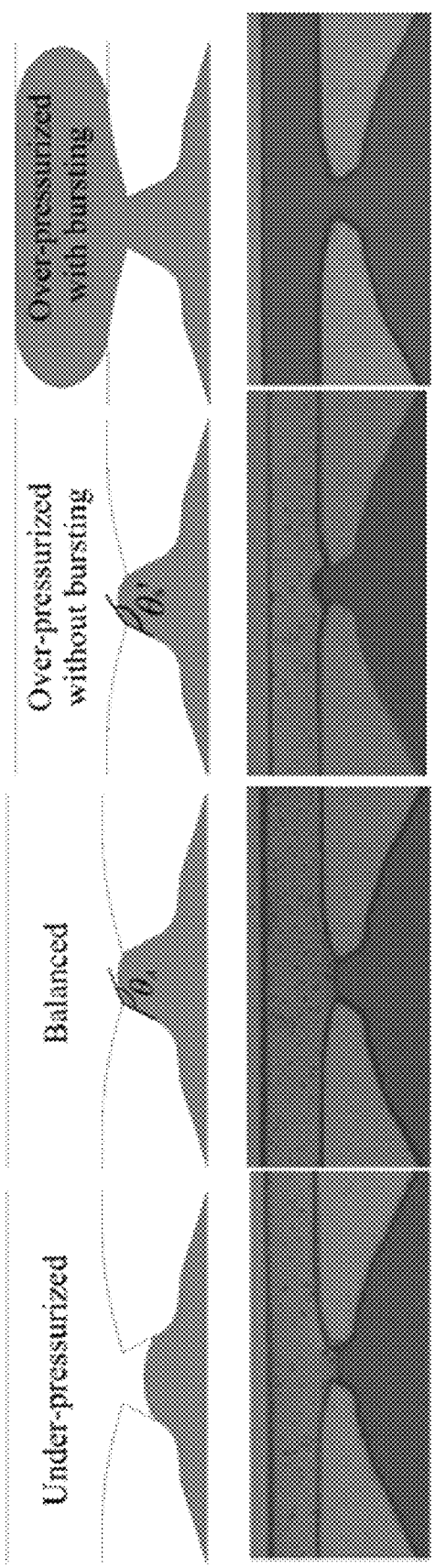
FIG. 8 is a panel of images and schematic drawings of gel-air interface under pressure.

Based on the relative relationship between the applied gel injection pressure and the Laplace pressure of the gel-air interface, the loaded gel can be directed to different locations of the perfusion microvalve with different interface curvatures (FIG. 8). For certain applications, it is necessary to confine the gel at a specific location with a well-controlled gel interface curvature. For example, a relatively flat gel interface is required for an endothelial cell monolayer to mimic a vessel wall.[15,20] With the addition of the pressure regulator module, it is possible to control the specific gel interface curvature positioned at the perfusion microvalve by designing a corresponding safety microvalve with a certain width.

Based on Young-Laplace equation, when gel bursting occurred at the safety microvalve, its burst pressure should be equal to the Laplace pressure at the perfusion microvalve with specific gel interface curvature. If these two valves were close enough, it could be formulated as:

$$\frac{\cos\theta^*_{A\text{-}safety}}{w_{safety}} = \frac{\cos\theta'_{s\text{-}perfusion}}{w_{perfusion}} (\theta_{A\text{-}perfusion} \leq \theta'_{s\text{-}perfusion} < \theta^*_{A\text{-}perfusion}) \quad (7)$$

where $\theta^*_{A\text{-}safety}$ and $\theta^*_{A\text{-}perfusion}$ are the critical bursting angles with the internal sidewall for safety microvalve and perfusion microvalve respectively $\theta_{A\text{-}perfusion}$ is the critical advancing contact angle with the internal sidewall for the perfusion microvalve, $\theta'_{s\text{-}perfusion}$ is the contact angle with the internal sidewall for the perfusion microvalve, and $w_{safety}$ and $W_{perfusion}$ are the widths of the safety microvalve and the perfusion microvalve, respectively. If the gel with a relatively flat interface (i.e. $\theta'_{s\text{-}perfusion}=\theta_{A\text{-}perfusion}$) is desired at the perfusion microvalve, the width of safety microvalve could be calculated by:

$$w_{safety} = \frac{\cos\theta^*_{A\text{-}safety}}{\cos\theta_{A\text{-}perfusion}} w_{perfusion} \qquad (8)$$

Cell Culture

For cell culture, human endothelial colony forming cell-derived endothelial cells (hECFC-ECs) were obtained from cord blood as previously described.[21] hECFC-ECs were selected and expanded on flasks coated with 10 μg mL$^{-1}$ fibronectin (Sigma Aldrich) in EGM-2 (Lonza) and transduced with mCherry-expressing lentiviral construct (LeGO-C2/Addgene plasmid: 27 339) to express fluorescence. Normal human lung fibroblasts (NHLF) were purchased from Lonza and expanded in 10% FBS DMEM (Corning). hECFC-ECs and NHLFs were used for experiments between passage 4 and 9 and cultured in a 37° C., 5% CO2, and 20% O2 incubator in 100% humidified air. Experimental set up for VMO in microfluidic platform was performed as previously described.[15] All experimental procedures were performed inside a Biosafety Level 2 laminar flow hood with sterile techniques.

Results and Discussion

Performance of the Pressure Regulator Under Different Flow Rates

Figure 3:
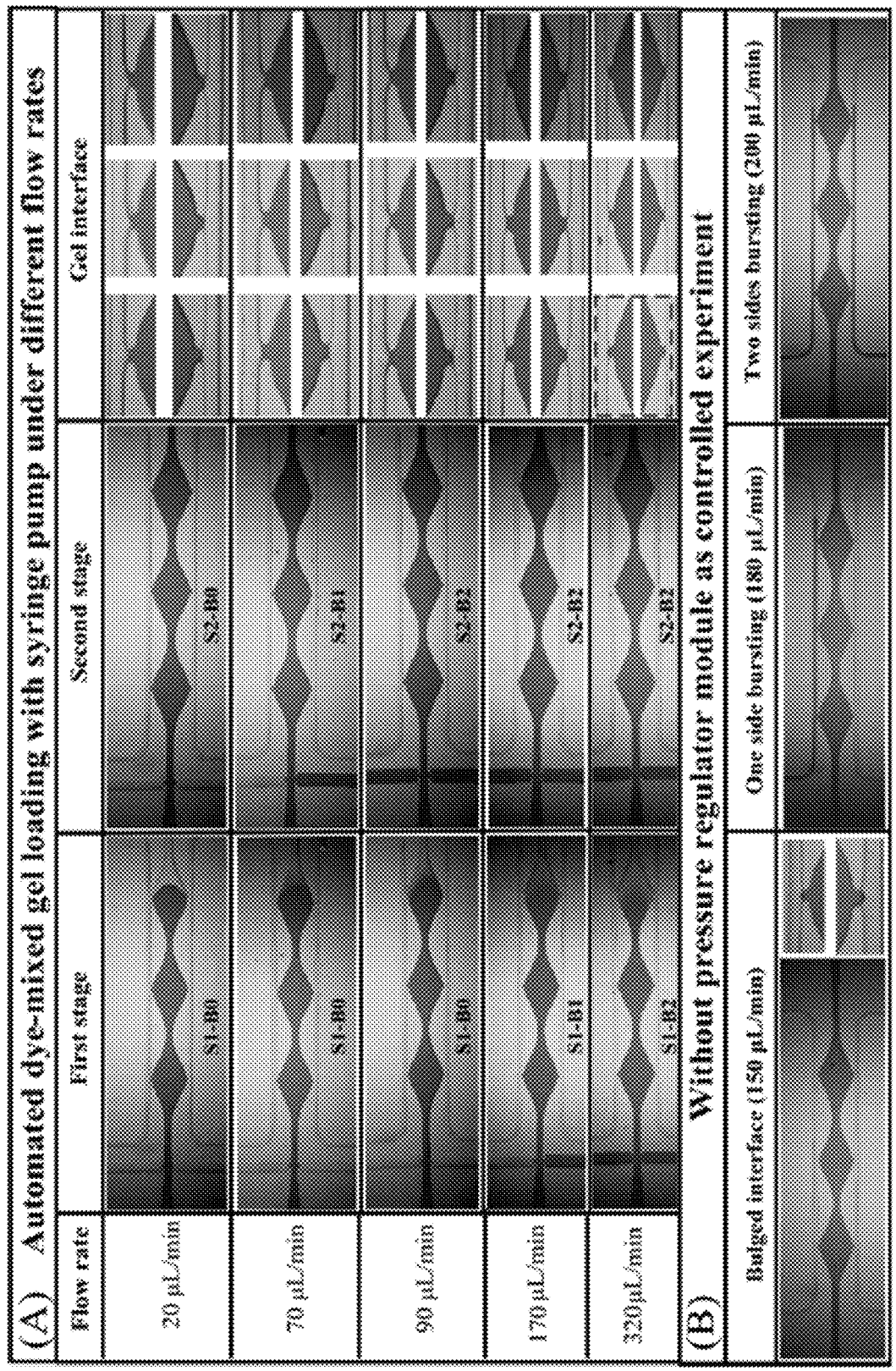
FIG. 3 is a panel showing pressure regulator performance. (3A) Performances of the pressure regulator at two stages by automated dye-mixed gel loading with syringe pump under different flow rates, and a well-controlled gel interface positioned at vertices of the perfusion microvalves. Dashed rectangle in gel interface column represents the slightly bulged gel interface at the high flow rate of 320 μL min$^{-1}$. (3B) Control experiment using the same gel loading channel without the pressure regulator module.
Figure 9:
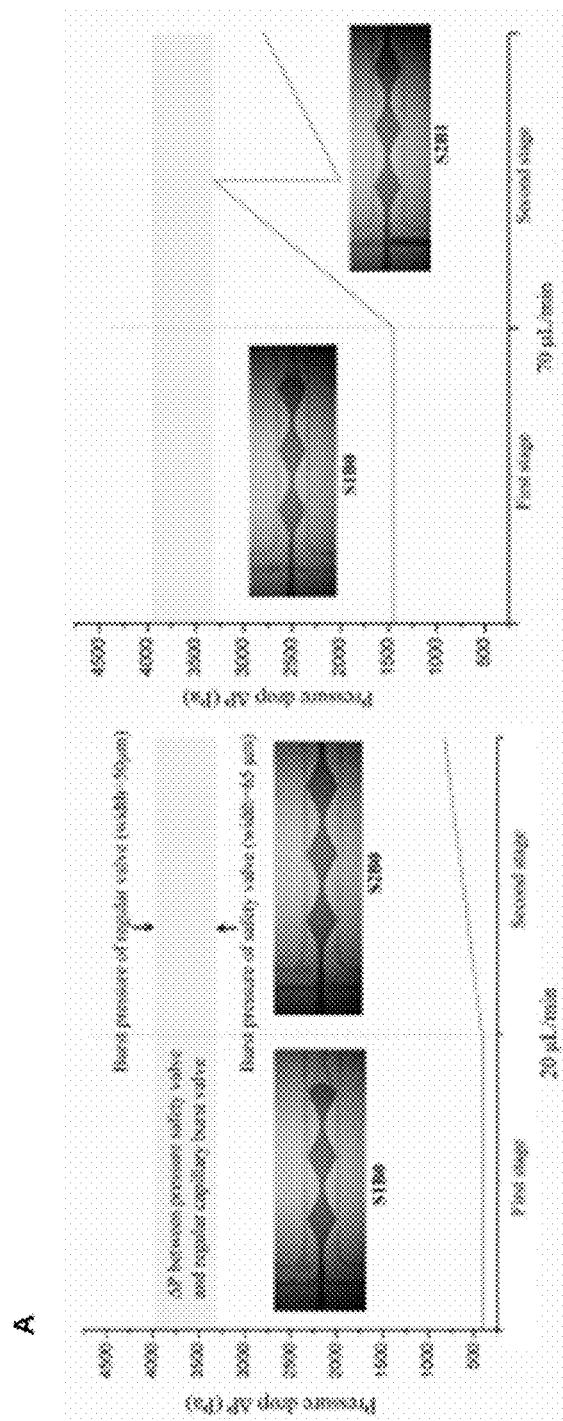
FIG. 9 is a panel showing hydraulic pressure profiles. (9A) Profiles 1 and 2 are shown; (9b) profiles 3 and 4 are shown; (9C) profile 5 is shown.
Figure 9:
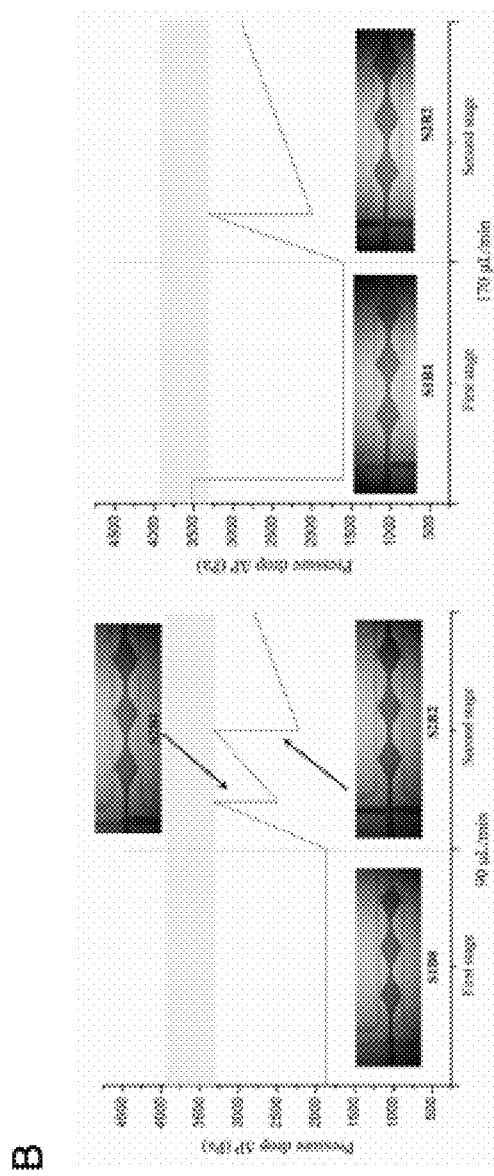
Figure 9:
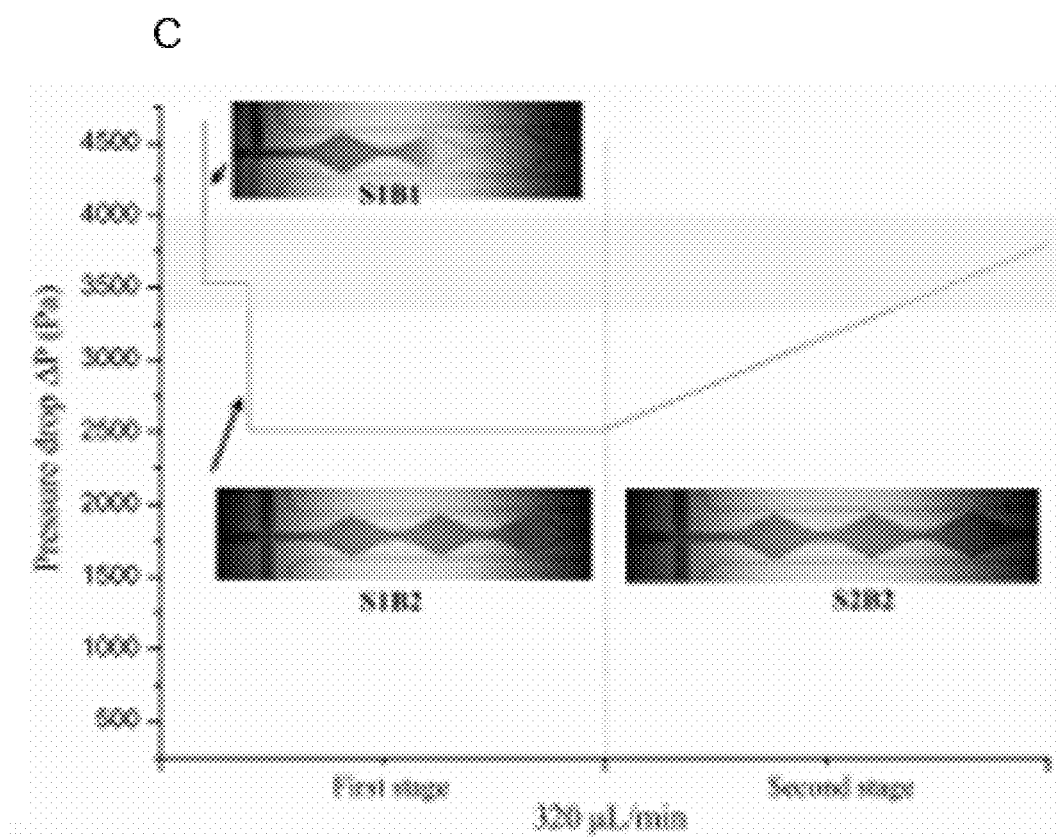

We first tested the performance of the pressure regulator module by automatic dye-mixed gel loading with a syringe pump under different flow rates, as shown in FIG. 3. In order to position the loaded gel at vertices of the perfusion microvalves with a non-bursting, relatively flat interface, the width of the safety microvalve ($w_{safety}$) was designed to be 65 μm by assuming $\theta^*_{A\text{-}safety}=180°$, $\theta_{A\text{-}perfusion}=140°$, and $w_{perfusion}=50$ μm. Therefore, the calculated burst pressure for the safety microvalve and the perfusion microvalve are 3318 Pa and 3983 Pa respectively (surface tension of water $\gamma=0.072$ N m$^{-1}$). As shown in FIG. 3A, when the applied flow rate was less than 90 μL min$^{-1}$, no gel bursting occurred at the safety microvalves of the pressure regulator module during the first stage (S1-B0). However, at the second stage, the hydraulic pressure inside the gel loading channel gradually built up with the increased fluidic resistance at the outlet reservoir. Once the hydraulic pressure surpassed the burst pressure of the safety microvalve, gel burst into one (S2-B1) or two (S2-B2) diversion channels to release the redundant gel. When the applied flow rate was higher than 170 μL min$^{-1}$, although the fluidic resistance remains constant during the first stage, gel bursting from one safety microvalve still occurred due to the high flow rate (S1-B1). At the second stage, the other safety microvalve also burst to release the built-up pressure resulting from the increased fluidic resistance. In all these cases, the gel interface at the perfusion microvalves maintained a relatively flat profile. However, when the applied flow rate was high (e.g. 320 μL min$^{-1}$), both safety microvalves burst during the first stage (S1-B2), which makes them no longer available to accommodate the second stage. To resolve this issue, a narrower (e.g. 55 μm or less) safety microvalve could be integrated into the pressure regulator module design. FIG. 9 in supplementary material shows more detailed information on the hydraulic pressure profile inside the gel loading channel at different stages under different flow rates. A control experiment was conducted by using the same gel loading channel without the pressure regulator module. As shown in FIG. 3B, when the applied flow rate was over 150 μL min$^{-1}$, the gel interface at the perfusion microvalves bulged until it finally burst into one or two adjacent microfluidic channels.

Sensitivity and Working Range for the Pressure Regulator

Figure 4:
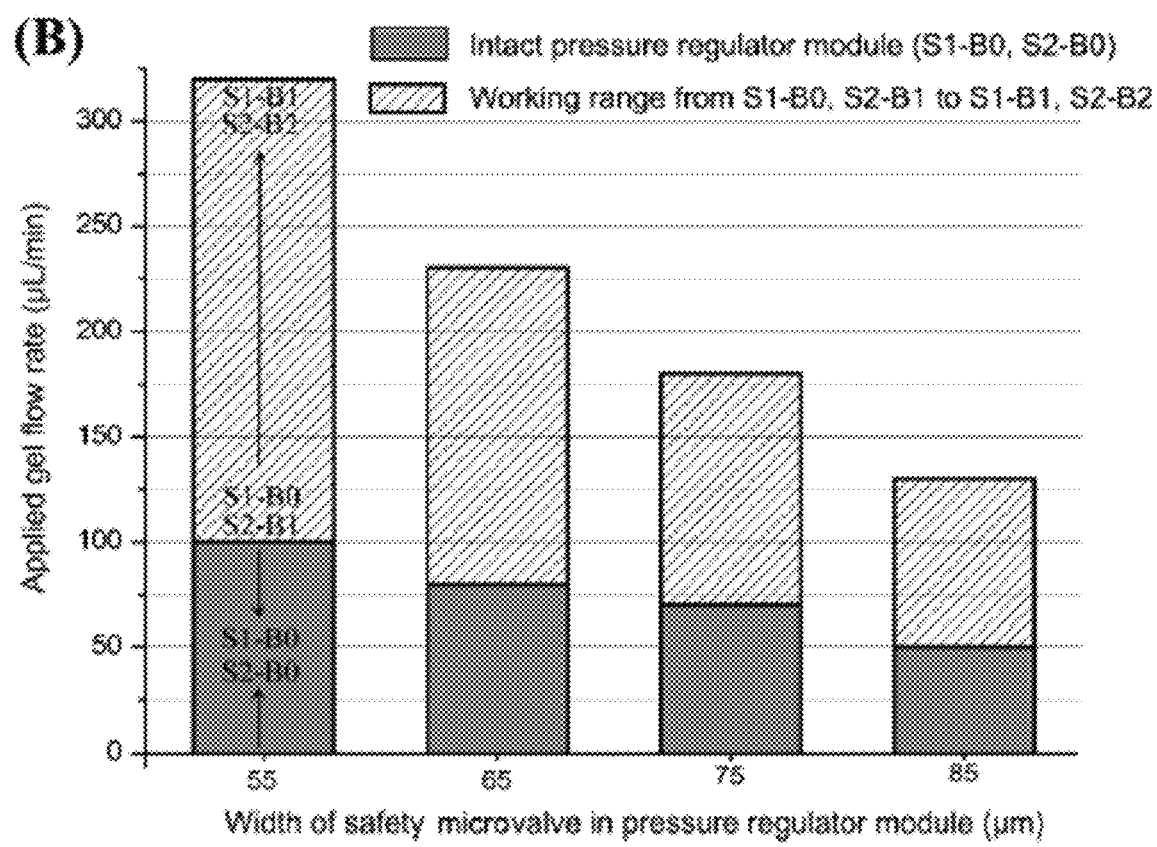
FIG. 4 is a panel showing results of gel loading experiments. (4A) Experimental results on dye-mixed gel loading using 55 μm and 85 μm wide safety microvalves at different flow rates. (4B) Comparison results for sensitivity and working range of the pressure regulator with different widths. The narrow safety microvalve has a large working range, while wide safety microvalves have high sensitivity.

FIG. 4A shows the dye-mixed gel loading performance with either 55 μm or 85 μm wide safety microvalves under different flow rates, respectively. In the device with the 85 μm wide safety microvalve, one safety microvalve burst to release pressure at the second stage under a flow rate as low as 50 μL min$^{-1}$ (S1-B0, S2-B1). At the same flow rate, both 55 μm wide safety microvalves were intact. The upper limit of the range for the 85 μm wide safety microvalve was 130 μL min$^{-1}$ (S1-B1, S2-B2). In contrast, the 55 μm wide safety microvalve was activated when the applied flow rate was increased to 100 μL min$^{-1}$ and its working limit was as high as 320 μL min$^{-1}$.

Thus, the sensitivity and working range for the pressure regulator module can be flexibly adjusted by the width of the safety microvalves. FIG. 4B showed the comparison results of the sensitivity and working range of safety microvalves with different widths, highlighting that the pressure regulator is more sensitive with wider safety microvalves. However, at the expense of sensitivity, the working range is inversely proportional to the microvalve width. Thus, there is a tradeoff between the sensitivity and working range for the pressure regulator module. Based on different needs and applications, either a narrow safety microvalve with large working range, or a wide safety microvalve with high sensitivity could be utilized.

For example, if a well-controlled gel interface curvature is desired, the pressure regulator module should be sensitive enough to release the build-up pressure rapidly, but this also requires the injection apparatus to operate with high accuracy to maintain a constant flow rate. If injection equipment is used that exhibits a large pressure fluctuation during injection, or a manual injection mode is utilized, then the pressure regulator module with a large working range should be used to ensure robust gel loading without bursting.

Gel Confinement Using Perfusion Microvalves with Wide Openings

Figure 10:
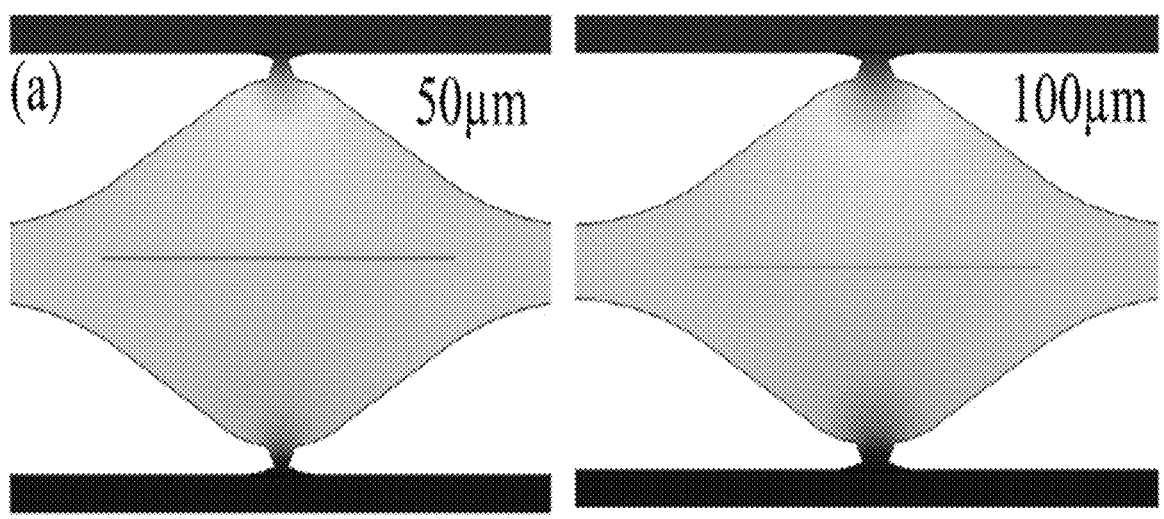
FIG. 10 is a panel comparing microvalves of difference widths. The panel shows: (10a) simulation results; (10b) corresponding interstitial flow velocity profiles; and (10c) vessel network formation.
Figure 10:
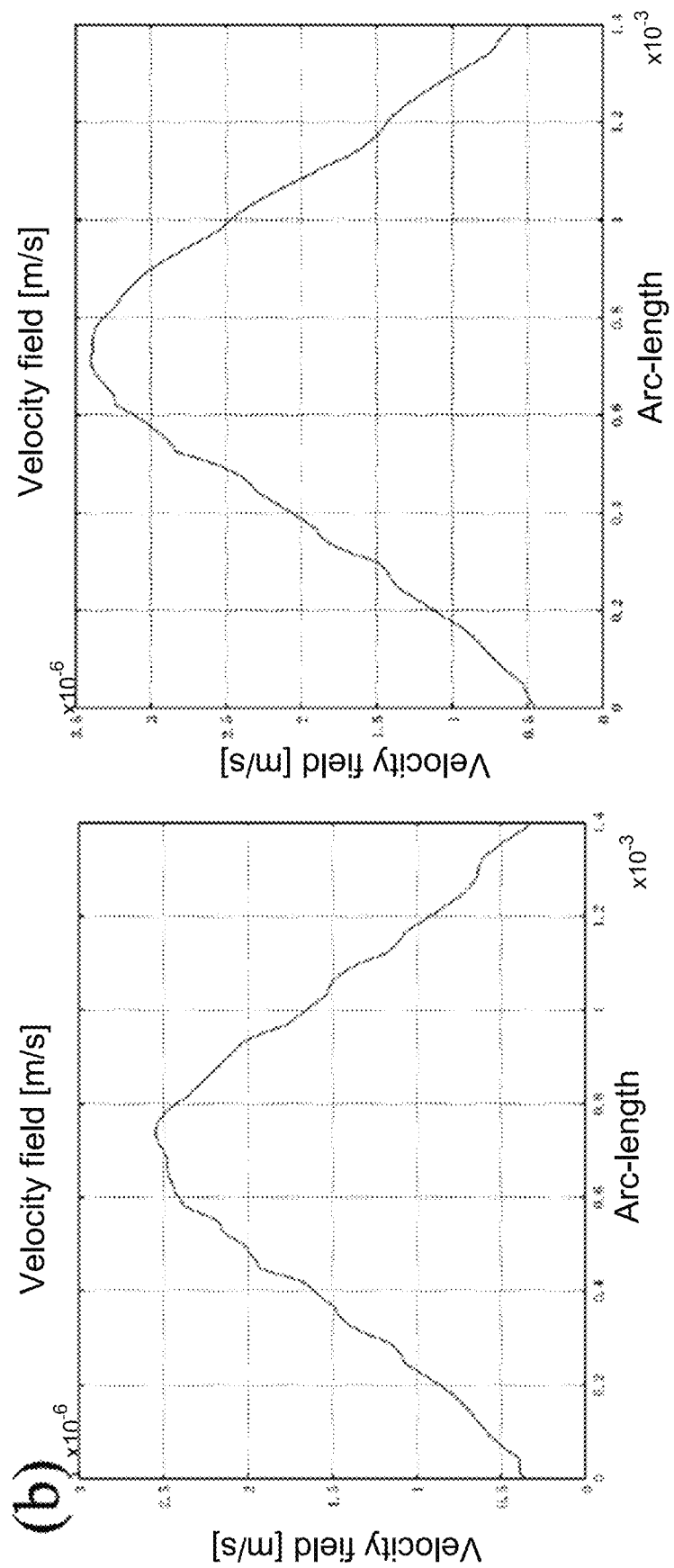
Figure 10:
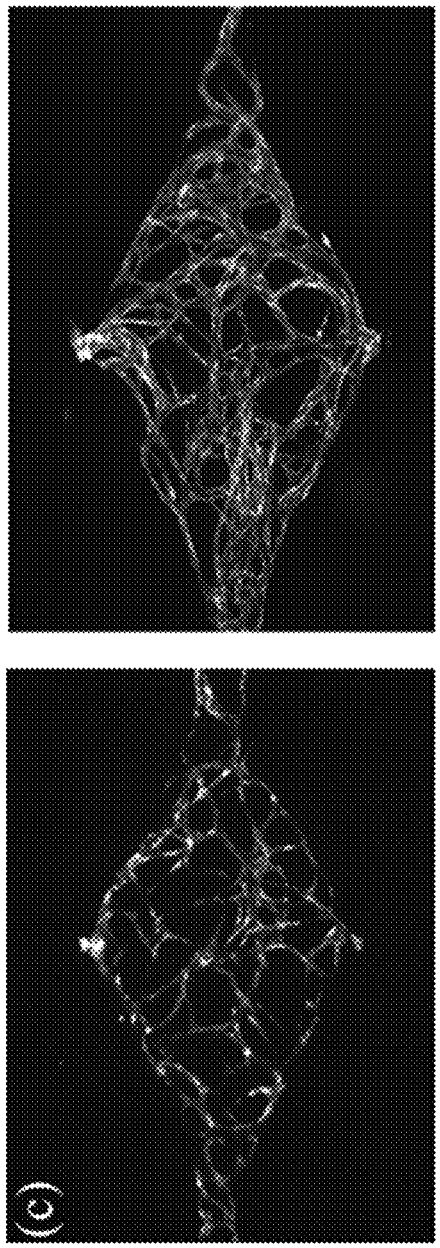

The width of the perfusion valve that connects the cell-containing gel matrix to the outer microfluidic channels (initially air-filled and then medium-filled) determines the rate at which biotransportation (convection) occurs across the gel. By integrating the pressure regulator module into the device it is possible to use wider perfusion microvalves while still retaining gel, thus allowing for greater rates of convection compared to narrower microvalves while maintaining the same hydrostatic pressure drop (FIG. 10). FIG. 5 shows the gel loading performance using 100 μm wide perfusion microvalves and 130 μm wide safety microvalves at different flow rates. The pressure regulator module was activated at a flow rate of 45 μL min$^{-1}$, and its upper limit was 70 μL min$^{-1}$. In comparison with the 50 μm wide perfusion microvalve, both the pressure regulator module and gel interface were sensitive to the change of applied flow rate. Once the flow rate was over 70 μL min$^{-1}$, two pressure safety microvalves burst at the first stage (S1-B2). An alternative e method to prevent gel bursting from the perfusion microvalves with wide openings under high flow rates would be to prevent or reduce pressure build-up with the increased fluidic resistance at the second stage. This could be achieved by changing the dispensed gel volume, as shown in FIG. 5. Here, only 10 μL dye-mixed gel was injected when the flow rate was over 70 µL min$^{-1}$. Because the fluidic resistance of the gel loading channel was less than that of the pressure regulator module, even though some gel was redirected into two diversion channels during the first stage, a large part of the injected gel flowed along the gel loading channel and filled up the tissue chambers. At a flow rate of 120 µL min$^{-1}$, bursting of two safety microvalves occurred earlier than that at flow rate of 70 µL min$^{-1}$ during the first stage, but they were still able to prevent gel bursting into the adjacent microfluidic channels. If more volume of medium is needed to supply sufficient mass transfer to sustain the cells, one can increase either the number of perfusion microvalves connected to each tissue chamber or the hydraulic pressure drop across the tissue chambers.

Manual Cell-Seeded Gel Loading with a Micropipettor

Figure 6:
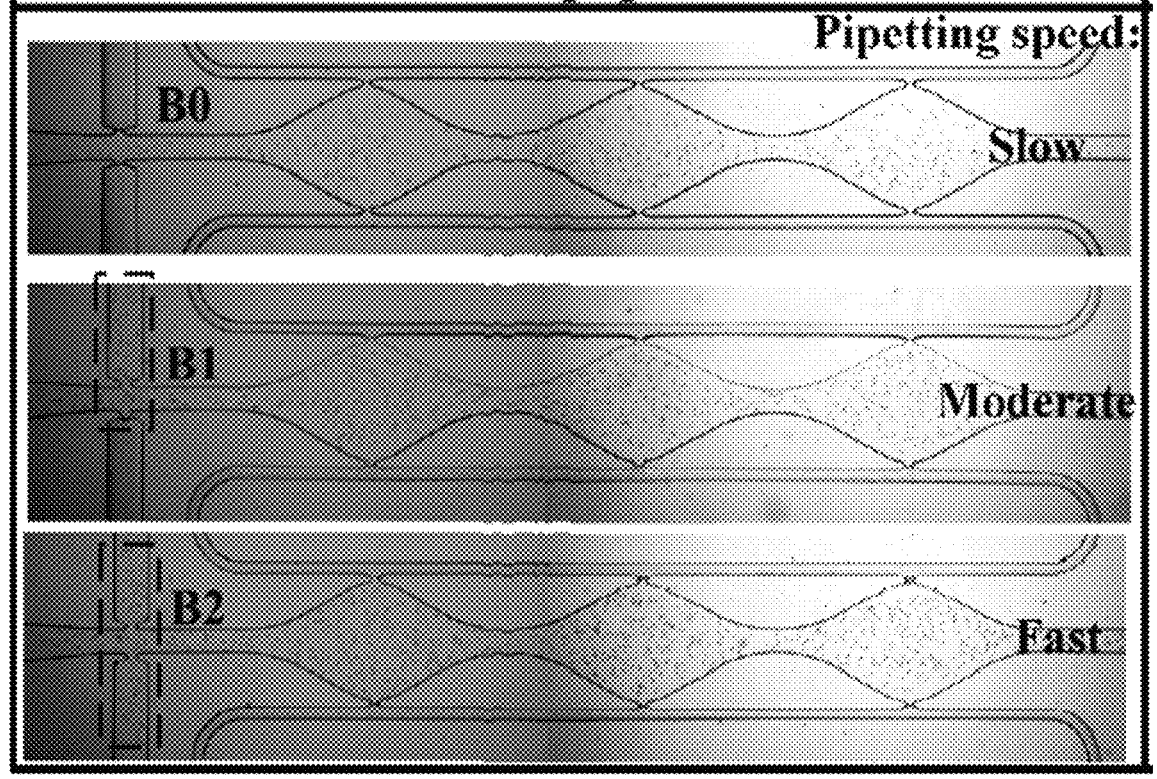
FIG. 6 is a panel of experimental results. (6A) Experimental results on manual cell-seeded fibrinogen gel loading with micropipettor under different pipetting speed. B0: no safety microvalve bursting, B1: bursting of one safety microvalve, and B2: bursting of two safety microvalves. Dashed rectangle represents the gel bursting region inside the pressure regulator module. (6B) Corresponding vessel network formation inside the microfluidic device after 7 days in culture.
Figure 6:
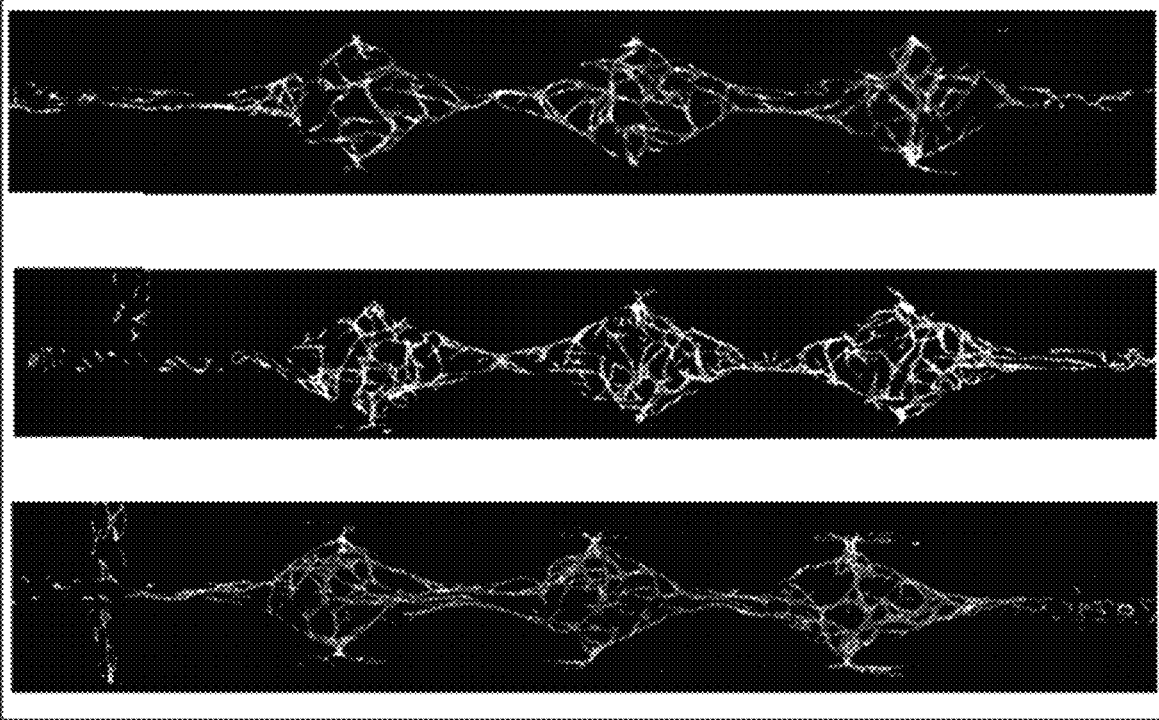

We further tested the performance of the pressure regulator module by manually loading the gel with a micropipettor. In this experiment we used our previously published VMO model to also confirm the biocompatibility of our design.[15] Human ECFC-ECs and NHLF were suspended in 10 mg mL$^{-1}$ fibrinogen solution and then quickly mixed with 50 U mL$^{-1}$ thrombin for a final concentration of 3 U mL$^{-1}$.[22] Since the polymerization time for fibrinogen after mixing with thrombin was short, it needed to be quickly injected into the gel loading channel. Therefore, it was difficult to operate the process fast enough using a syringe pump. Regardless of the pipetting speed manually applied to the micropipettor, the pressure regulator module effectively prevented gel bursting similar to the experimental results of dye-mixed gel loading with the syringe pump, as shown in FIG. 6A. When the slow pipetting speed was applied on push-button, no gel bursting occurred at the pressure regulator module. When the fast pipetting speed was applied, one or two safety microvalves burst to release the hydraulic pressure inside the tissue chambers to prevent gel bursting out of the perfusion microvalves. FIG. 6B shows the successfully-formed 3D VMO after 7 days in culture in the microfluidic device using different loading force and bursting conditions.

Figure 7:
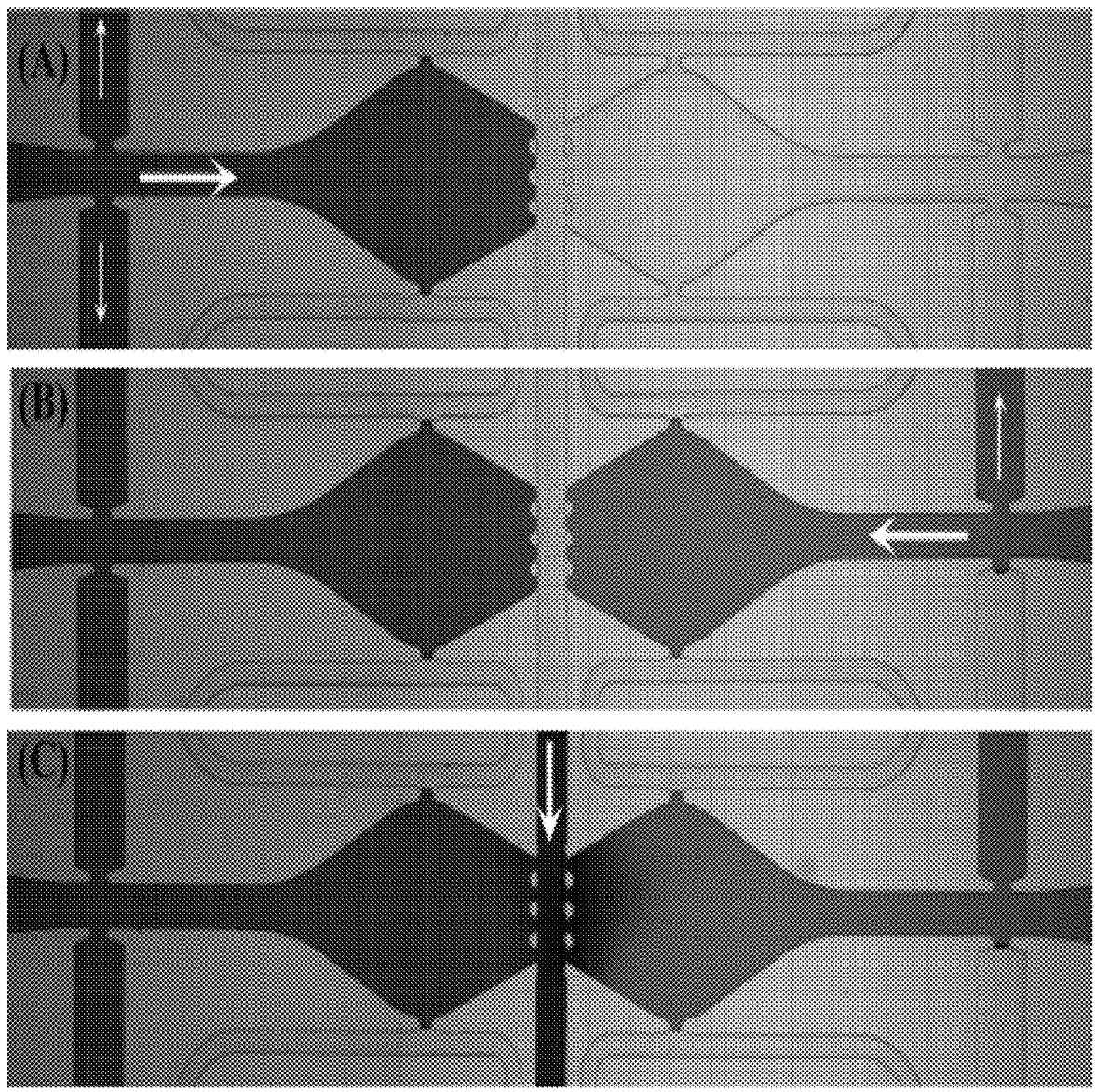
FIG. 7 is a panel showing heterotypic dye-mixed gel loading into a microfluidic device with a pressure regulator module at each end serving as a gel loading outlet. (7A) Step 1: green dye-mixed gel loading into left chamber and bursting of two safety microvalves. (7B) Step 2: red dye-mixed gel loading into right chamber and bursting of only one safety microvalve. (7C) Step 3: blue dye-mixed gel loading into central connecting channel to connect the two (green and red) chambers. Diffusion between the chambers then occurred.
Figure 11:
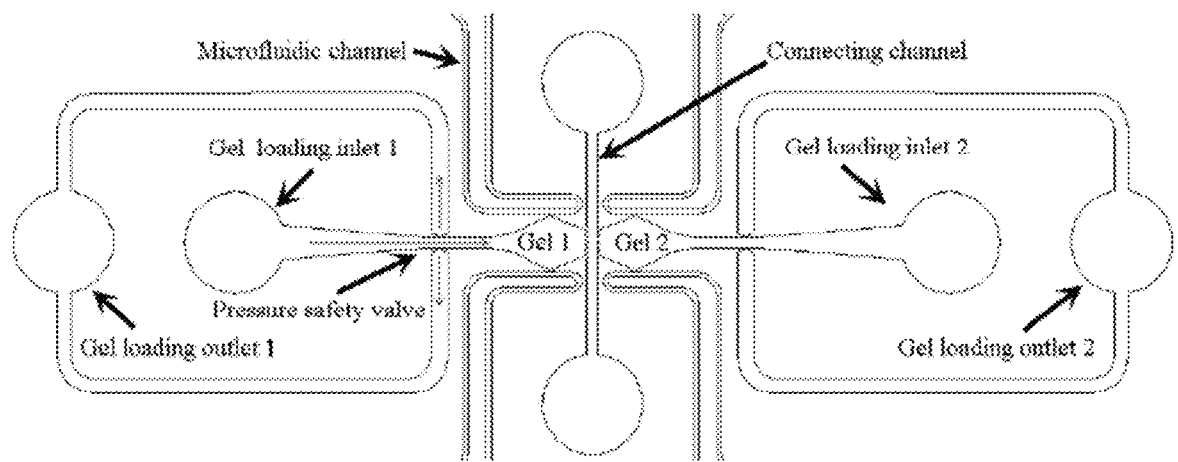
FIG. 11 is an embodiment of a chip design.
Figure 12:
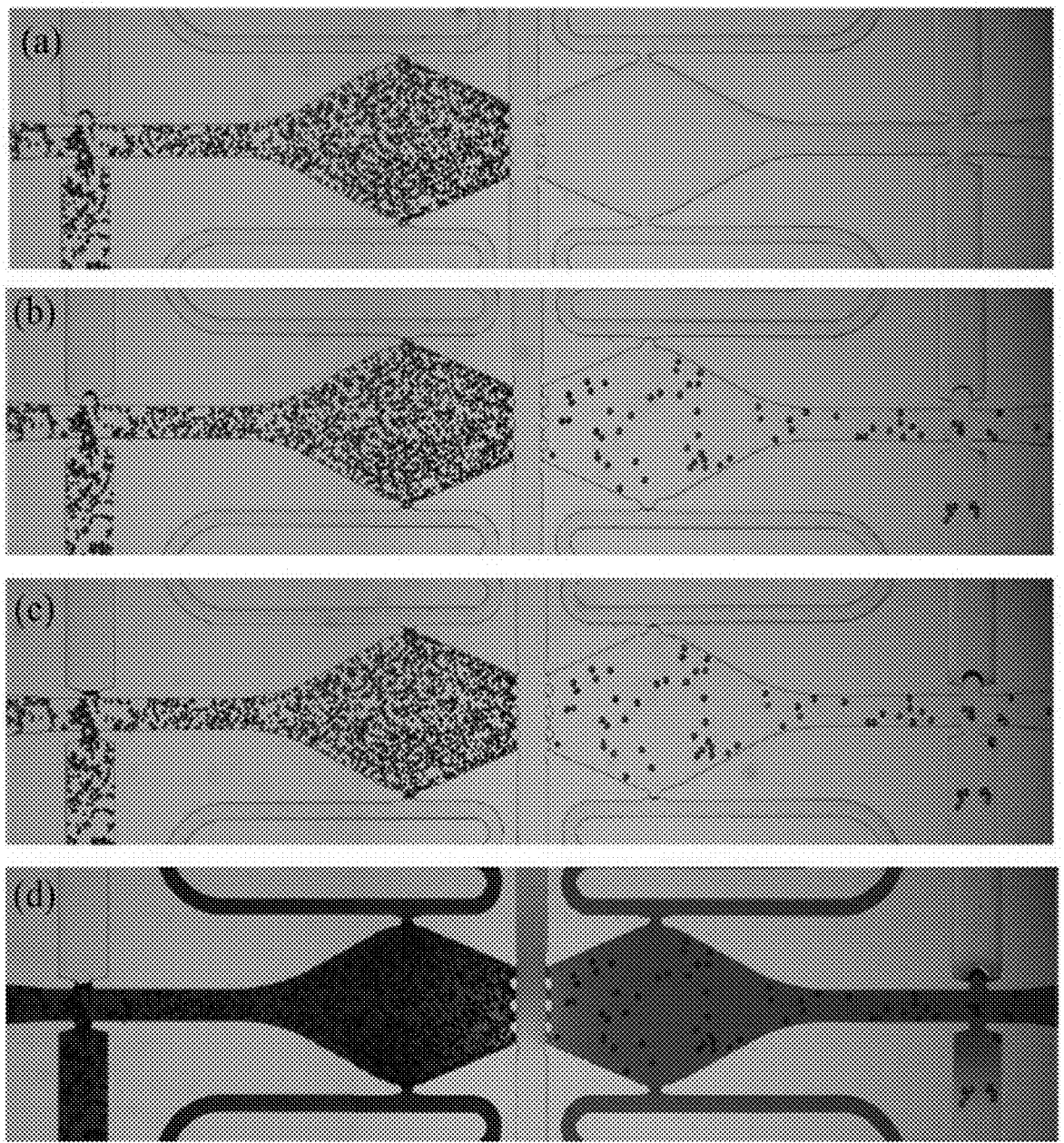
FIG. 12 is a panel showing results of gel loading. Different particles are shown under different conditions (12a-12d).

Independent Gel Loading and Microenvironment Control of Interconnected Tissue Chambers There is considerable interest in connecting organ-on-chip modules (e.g. liver and gut for metabolic studies or colon and lung for metastasis studies), however, the mechanics of this are still being explored. Here we show that use of the pressure regulator module can facilitate heterotypic gel confinement inside a microfluidic device with interconnected structures (FIG. 7). A gel loading inlet and a pressure regulator module as gel loading outlet can be integrated at each end of the tissue chamber, allowing for individual loading of each compartment without bursting into the central connecting channel. The connecting channel can then be loaded at a later time to facilitate connection between the two halves (FIGS. 7, 11). Our design differs from previously reported chip designs for heterotypic gel loading that cannot realize the independent microenvironment control,[6,11] and has the advantage of increased flexibility. FIG. 12 shows that each tissue chamber can be separately loaded with different particles mixed in the gel to mimic cells, and perfused with different liquid dyes, mimicking independent microenvironment control. This design can be used for multi-tissue co-culture, tumor angiogenesis, and human body-on-chip drug screening applications.

Conclusion

The inventors present a novel on-chip pressure regulator module design that facilitates robust, reproducible, non-bursting hydrogel injection. The build-up pressure under different gel loading stages induced by redundant gel can be released by the activation of the pressure regulator module, once the hydraulic pressure inside the gel loading channel is higher than the safety microvalve burst pressure of the pressure regulator module. Furthermore, it can generate a well-controlled gel interface at a specific location in the perfusion microvalves under a wide range of flow rates. Due to its simple design, the pressure regulator module can be integrated into any microfluidic device that requires various types of hydrogel loading. In addition, both the sensitivity and working range of the pressure regulator module can be flexibly adjusted by changing the width of the safety microvalves according to specific applications. The pressure regulator module also allows for confining gels at perfusion microvalves with wide openings. Experiments on dye-mixed gel loading with a syringe pump and cell-seeded gel loading with a micropipettor demonstrate the module's compatibility with versatile liquid handling apparatuses operated in either automatic or manual mode. The pressure regulator module design is versatile and enables designs that require placement of heterotypic tissue culture gels and microfluidic channels in different arrangements. It should prove useful for multi-organ-on-chip platforms.

Discussion

By integrating a pressure regulator module into our micro-fluidic platform (3D-VMO model) we can effectively prevent gel bursting from the tissue chambers to the adjacent micro-fluidic channels. The device operates on a single microfluidic layer and maintains a well-controlled gel interface under different flow rates. This design has greatly facilitated reliable and reproducible loading of gels into the device as the steep learning curve required for successful manual loading is now obviated—any overpressure by the operator is efficiently suppressed as gel is diverted to the overflow to prevent bursting of the air-gel interface. The device also allows us to control the size and characteristics of the air-gel interface, which is critical for controlling the rate of convection, and is also important for applications requiring seeding of monolayer cells into the outer microfluidic channels.

For a multi-tissue communication device, two different hydrogels or the same hydrogel containing a different cell population need to be injected sequentially into the interconnected tissue chambers with independent microenvironment control. We have shown how this is possible using a modified design with the integration of pressure regulator module as gel loading outlet (FIG. 7). However, since the hydrogels inside each compartment are interconnected and become one unit, the fluidic resistance of the whole tissue chamber will increase greatly and this can affect the perfusion performance (e.g. interstitial flow velocity or profile, etc.) inside the tissue chamber.[23] In order to maintain uniform and well-controlled perfusion it might be beneficial to separate the fluidic channel and multi-tissue co-culture chambers into different layers. In this case it will be necessary to prevent the individual injected gel inside its respective tissue chamber from bursting both horizontally and vertically, which can also be realized with the assistance of pressure regulator module. Here, the safety microvalve burst pressure of the regulator module should be less than both the advancing pressure between different layers and the burst pressure between the interconnected tissue chambers in different rows.

EXAMPLE 2

FIG. 8 shows the different gel loading condition based on the relative pressure values between applied gel injection pressure and Laplace pressure of gel-air interface at perfusion microvalve. If gel injection pressure is equal to the balanced pressure ($P_b$) with the critical advancing contact angle of $\theta_A$ between the interface and internal sidewall, the gel will be positioned at the vertices of perfusion microvalve with gently sloping interface (Balanced). However, when the applied gel injection pressure is not strong enough, the loaded gel will only fill a portion of perfusion microvalve (Under-pressurized). In contrast, when the gel injection pressure is over Pb but less than the burst pressure of perfusion microvalve $P_{valve-burst}$, the gel interface will bulge to the contact angle of $\theta_s'$ ($\theta_A < \theta_s' < \theta_A^*$) with the internal sidewall (Overpressurized without bursting). Once the contact angle of gel interface with the internal sidewall is above the critical bursting contact angle $\theta_A^*$, the gel will burst into the adjacent microfluidic channel (Over-pressurized with bursting).

Hydraulic pressure profile inside gel loading channel at different stages under different flow rates is shown in FIG. 9. Referring to FIG. 9A): (1) Due to the low flow rate of 20 µL/min, the hydraulic pressure inside gel loading channel was much less than the burst pressure of safety microvalve in the pressure regulator module regardless of stage. Therefore, both safety microvalves would be intact at both the first stage (S1B0) and the second stage (S2B0). (2) During the first stage under the flow rate of 70 µL/min, the hydraulic pressure inside gel loading channel was less than the burst pressure of safety microvalve. Therefore, there was no bursting occurred at this stage (S1B0). However, due to the increased fluidic resistance at the second stage, the hydraulic pressure inside gel loading channel would increase accordingly. Once it reached up to the burst pressure of safety microvalve, one would burst first to redirect redundant gel to release the build-up pressure (S2B1). Although certain amount of gels were directed to the diversion channel, a portion of gels would still flow towards the outlet reservoir of gel loading channel. The relative value of gel volume towards diversion channel and gel loading channel depended on the relative fluidic resistance values between diversion channel with safety valves and gel loading channel with certain height medium inside outlet reservoir, respectively. Since certain volume of gel flowed into the diversion channel, the flow rate inside the gel loading channel would reduce. Even though the total fluidic resistance including the gel loading channel and outlet reservoir still increased, the build-up rate of hydraulic pressure inside gel loading channel would become slow without reaching the burst pressure of safety microvalve again. Referring to FIG. 9B: (3) When flow rate reached up to 90 µL/min, two safety microvalves would burst one by one during the second stage. Firstly, one safety microvalve would burst to release the build-up hydraulic pressure (S2B1), just like the process at the flow rate of 70 µL/min. Due to the increased flow rate from 70 µL/min to 90 µL/min, the build-up rate of hydraulic pressure inside gel loading channel became a little bit faster than that of 70 µL/min. Therefore, the hydraulic pressure inside gel loading channel would increase to burst pressure of safety microvalve again, which would induce the bursting of the other one (S2B2) to release the build-up pressure. (4) If the flow rate of 170 µL/min was applied, its initial hydraulic pressure was over the burst pressure of safety microvalve, which would induce the bursting of one safety microvalve at the first stage (S1B1). Therefore, the flow rate would decrease accordingly to decrease the hydraulic pressure inside gel loading channel. At the second stage, the other one would burst to release the pressure due to the increased fluidic resistance, just like the process of 70 µL/min at the second stage. Referring to FIG. 9C: (5) If the applied flow rate was pretty high (e.g. 320 µL/min), one pressure safety microvalve would burst first to release the initial hydraulic pressure during the first stage (S1B1). However, the hydraulic pressure inside gel loading channel after releasing was still higher than the burst pressure of safety microvalve, then the other one would burst immediately at the first stage (S1B2). At the second stage, the hydraulic pressure inside gel loading channel would increase continuously because both safety valves were invalid during the second stage. If the hydraulic pressure value inside gel loading channel was between the burst pressure of safety microvalve and burst pressure of perfusion microvalve, the gel interface pinned at the perfusion microvalve would bulge without bursting.

In FIG. 10, comparison results of perfusion microvalve with different widths are shown (Left: 50 µm VS Right: 100 µm). (10a) Simulation results on pressure distribution inside tissue chamber under the same hydrostatic pressure drop (5 mm $H_2O$). (10b) The corresponding interstitial flow velocity profile in the middle of tissue chamber horizontally. Since more bulk flow of culture medium transported across the tissue chamber with 100 µm wide perfusion microvalve under the same hydrostatic pressure drop, its interstitial flow velocity was higher than that with 50 µm width. (10c) Vessel network formation inside tissue chamber. The anastomosed vessel at the 100 µm perfusion microvalve was wider than that of 50 µm perfusion microvalve, which was beneficial to particle/cell perfusion into vessel lumen.

FIG. 11 shows a schematic of a chip design for heterotypic hydrogel injection along gel loading direction by using the diversion outlet in the pressure regulator module as a gel loading outlet. Since the burst pressure of safety microvalve in the pressure regulator is smaller than those of perfusion microvalves in the tissue chamber, the pressure regulator will burst first to release the redundant gel as gel loading outlet. The central connecting channel can be injected with either gel to interconnect these two heterotypic gels for multi-tissue co-culture study or liquid (medium, drug, etc.) for drug screening application.

FIG. 12 shows experimental results on gel loading into each tissue chamber with different particles and independent microenvironment control. (12a) Loading the left chamber with 25 µm beads in fibrin gel. (12b) Loading the right chamber with 45 µm beads in fibrin gel. (12c) Loading the central connecting channel with pure fibrin gel to interconnect these two chambers. (12d) Loading the microfluidic channel with food dye (green on the left, red on the right) independently and perfusion into their respective tissue chambers.

REFERENCES

The following publications are incorporated by reference herein in their entirety:

1 D. H. Lee, C. Y. Bae, S. Kwon and J. K. Park, Lab Chip, 2015, 15(11), 2379.
2 V. Vickerman, J. Blundo, S. Chung and R. Kamm, Lab Chip, 2008, 8(9), 1468.
3 C. Y. Chan, P.-H. Huang, F. Guo, X. Ding, V. Kapur, J. D. Mai, P. K. Yuen and T. J. Huang, Lab Chip, 2013, 13(24), 4697.
4 S. N. Bhatia and D. E. Ingber, Nat. Biotechnol., 2014, 32(8), 760
5 D. Huh, Y. S. Torisawa, H. J. Kim and D. E. Ingber, Lab Chip, 2012, 12(12), 2156.
6 S. Kim, H. Lee, M. Chung and N. L. Jeon, Lab Chip, 2013, 13(8), 1489.

7 Y. Zheng, J. Chen, M. Craven, N. W. Choi, S. Totorica, A. Diaz-Santana, P. Kermani, B. Hempstead, C. Fischbach-Teschl and J. A. López, Proc. Natl. Acad. Sci. U.S.A, 2012, 109(24), 9342.

8 Y. H. Hsu, M. L. Moya, C. C. Hughes, S. C. George and A. P. Lee, Lab Chip, 2013, 13(1), 81.

9 Y. H. Hsu, M. L. Moya, C. C. Hughes, S. C. George and A. P. Lee, Lab Chip, 2013, 13(15), 2990.

10 J. H. Yeon, H. R. Ryu, M. Chung, Q. P. Hu and N. L. Jeon, Lab Chip, 2012, 12(16), 2815.

11 M. B. Chen, J. A. Whisler, J. S. Jeon and R. D. Kamm, Integr. Biol., 2013, 5(10), 1262.

12 C. P. Huang, J. Lu, H. Seon, A. P. Lee, L. A. Flanagan, H. Y. Kim, A. J. Putnam and N. L. Jeon, Lab Chip, 2009, 9(12), 1740.

13 A. K. Au, H. Lai, B. R. Utela and A. Folch, Micromachines, 2011, 2(2), 179.

14 M. L. Moya, Y. H. Hsu, A. P. Lee, C. C. Hughes and S. C. George, Tissue Eng., Part C, 2013, 19(9), 730.

15 X. Wang, D. T. Phan, A. Sobrino, S. C. George, C. C. Hughes and A. P. Lee, Lab Chip, 2016, 16(2) 282.

16 M. Rhee, Y. K. Light, S. Yilmaz, P. D. Adams, D. Saxena, R. J. Meagher and A. K. Singh, Lab Chip, 2014, 14(23), 4533.

17 K. W. Oh, K. Lee, B. Ahn and E. P. Furlani, Lab Chip, 2012, 12(3), 515.

18 D. J. Beebe, G. A. Mensing and G. M. Walker, Annu. Rev. Biomed. Eng., 2002, 4(1), 261.

19 H. Cho, H. Y. Kim, J. Y. Kang and T. S. Kim, J. Colloid Interface Sci., 2007, 306(2), 379.

20 I. K. Zervantonakis, S. K. Hughes-Alford, J. L. Charest, J. S. Condeelis, F. B. Gertler and R. D. Kamm, Proc. Natl. Acad. Sci. U.S.A, 2012, 109(34), 13515.

21 J. M. Melero-Martin, Z. A. Khan, A. Picard, X. Wu, S. Paruchuri and J. Bischoff, Blood, 2007, 109(11), 4761.

22 M. L. Moya, Y.-H. Hsu, A. P. Lee, C. C. W. Hughes and S. C. George, Tissue Eng., 2013, 19(9), 730.

23 L. F. Alonzo, M. L. Moya, V. S. Shirure and S. C. George, Lab Chip, 2015, 15(17), 3521.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the invention and the following claims.

What is claimed is:

1. A chip-based microfluidic platform comprising:
   a pressure regulator module;
   one or more tissue chambers containing flowable material comprising hydrogel or hydrogel precursor, each having an inlet at a first end and an outlet at a second end, and opposing sides between the first and second ends;
   two or more tissue chamber capillary burst valves each having a burst pressure and configured to have a first function of preventing hydrogel or hydrogel precursor from bursting into at least one of the microfluidic channels and a second function for perfusing nutrients through at least one or more of the tissue chambers, the tissue chamber capillary burst valves located between the first and second ends of each tissue chamber and connected to and directly through respective sides of said one or more tissue chambers; and
   microfluidic channels located parallel to and fluidly connected to said one or more tissue chambers via said two or more tissue chamber capillary burst valves, the chip-based microfluidic platform comprising said inlet connected to the first end of the one or more tissue chambers and said outlet connected to the second end of the one or more tissue chambers;
   the pressure regulator module comprises a pressure regulator module outlet;
   a pressure safety capillary burst valve on the pressure regulator module having a burst pressure lower than the lowest burst pressure of the two or more tissue chamber capillary burst valves;
   a bypass channel fluidly connected via the pressure safety capillary burst valve to the chip-based microfluidic platform inlet upstream of the one or more tissue chambers to prevent pressure build-up in the one or more tissue chambers above the lowest pressure safety capillary burst valve burst pressure; and
   one or more reservoirs;
   an outlet on the pressure regulator module fluidly connecting the bypass channel to the one or more reservoirs.

2. The chip-based microfluidic platform of claim 1, wherein the one or more tissue chambers contains flowable material comprising a cell-hydrogel mixture.

3. The chip-based microfluidic platform of claim 1, wherein the hydrogel or hydrogel precursor forms an air-flowable material interface at each capillary burst valve of the tissue chambers, and wherein diversion of flowable material into the reservoirs maintains each interface.

4. The chip-based microfluidic platform of claim 1, wherein each capillary burst valve width affects the sensitivity and working range of the pressure regulator.

5. The chip-based microfluidic platform of claim 1, wherein said one or more tissue chambers comprises a plurality of serially connected tissue chambers.

* * * * *